US008664610B2

(12) United States Patent
Chuang

(10) Patent No.: US 8,664,610 B2
(45) Date of Patent: Mar. 4, 2014

(54) SINGLE PHOTON EMISSION COMPUTED TOMOGRAPHY INSTRUMENT AND THE OPERATING METHOD THEREOF

(75) Inventor: Keh-Shih Chuang, Hsinchu (TW)

(73) Assignee: Industrial Technology Research Institute, Hsin-Chu (TW)

( * ) Notice: Subject to any disclaimer, the term of this patent is extended or adjusted under 35 U.S.C. 154(b) by 43 days.

(21) Appl. No.: 13/282,204

(22) Filed: Oct. 26, 2011

(65) Prior Publication Data

US 2013/0015359 A1    Jan. 17, 2013

(30) Foreign Application Priority Data

Jul. 15, 2011   (TW) .............................. 100125062 A

(51) Int. Cl.
*G01T 1/166*   (2006.01)
(52) U.S. Cl.
USPC .................................................... 250/363.04
(58) Field of Classification Search
USPC .............. 250/363.03, 363.04, 363.08, 370.09
See application file for complete search history.

(56) References Cited

U.S. PATENT DOCUMENTS

| 4,664,890 | A | 5/1987 | Tawada et al. |
| 6,225,631 | B1 | 5/2001 | Mastrippolito et al. |
| 6,921,902 | B2 * | 7/2005 | Chuang et al. ........... 250/363.03 |
| 7,491,941 | B2 | 2/2009 | Olden et al. |
| 2011/0103544 | A1 * | 5/2011 | Hermony ........................ 378/19 |

FOREIGN PATENT DOCUMENTS

| TW | I269054 | 12/2006 |
| TW | M355091 | 4/2009 |
| TW | 201041559 A | 12/2010 |

* cited by examiner

*Primary Examiner* — David Porta
*Assistant Examiner* — Faye Boosalis
(74) *Attorney, Agent, or Firm* — Birch, Stewart, Kolasch & Birch, LLP

(57) ABSTRACT

A single photon emission computed tomography instrument is provided, which has a platform, at least one detector, at least one beam stopper, a signal processing device and a computer. The at least one detector is disposed at one side of the platform, and the at least one beam stopper is disposed between the platform and the detector. The signal processing device is electrically communicated with the at least one detector, and the computer is electrically communicated with the signal processing device. The present disclosure further provides an operating method which the beam stopper is added or removed respectively while scanning an analyze by the single photon emission computed tomography instrument in different angles. The projection dataset emitted from the focus could be estimated by subtracting the projecting data without the beam stopper from that with the beam stopper, and high resolution image could be obtained by using image reconstruction program.

15 Claims, 7 Drawing Sheets

SINGLE PHOTON EMISSION COMPUTED TOMOGRAPHY INSTRUMENT AND THE OPERATING METHOD THEREOF

TECHNICAL FIELD

The present disclosure relates to a single photon emission computed tomography (SPECT) instrument and the operating method thereof, and more particularly, to a single photon emission computed tomography instrument operated basing upon the use of beam stoppers for absorbing beams of radiation.

TECHNICAL BACKGROUND

The application of single photon emission computed tomography (SPECT) technique in molecular imaging is becoming more and more popular, as it can be performed without requiring any accelerator and also it can produce required images in an instant manner, due to the radioisotope that is commonly used by SPECT imaging has a comparatively longer half-life period. Recently, SEPCT scanner is becoming the essential instrument for many animal studies relating to internal orgasm whichever requires sharp images with very accurate spatial and contrast resolutions.

Conventionally, the animal SPECT scanner is generally configured with pinhole collimator, which is made of a material of high atomic number and high density based on the fact that beams of radiation are better absorbed by materials with high atomic number and high density. Therefore, SPECT scanner using pinhole collimator can be very expensive, not to mention that it can be very difficult to manufacture. In addition, in order to acquire SPECT images, either the pinhole collimator and the detector of the SPECT scanner are rotated around an object to be scanned in a circular orbit or the scanned object is enabled to rotate with respect to the pinhole collimator and the detector, and thereby, projections are acquired at defined points during the rotation, typically every 3-6 degrees. In most cases, a full 360-degree rotation is used to obtain an optimal reconstruction. However, in a situation when the pinhole collimator is enabled to rotate about the scanned object in a circular orbit for acquiring projections, it is more than often that there are ghost artifacts appeared on the recontruction image due to certain mechanical assembly inaccurqacy as the pinhole collimator can be very heavy.

There are already many studies available for reducing the aforesaid image noises that are generated due to poorly calibrated pinhole collimator in orbital movement. One of which is a SPECT system based on a static triangular detector setup, with a tungsten cylindric imaging cavity in the center and 75 gold micropinhole apertures in the cavity wall. The pinholes that are evenly distributed into multiple rings on the cavity wall are focused on the center of an interested field-of-view (FOV) where the scanned object is disposed. Operationally, detectors are orientated for acquiring gamma rays that travel passing through the pinholes so as to be used in SPECT image reconstruction. As the pinhole collimator is built like a cylindric imaging cavity, the scanned object can be placed inside the cylindric pinhole collimator while allowing the pinholes that are formed on the cavity wall to be arranged surrounding the scanned object. Thereby, to acquire SPEACT images, neither the scanned object nor the pinhole collimator and detectors are being driven to rotate in any way, and also the aforesaid SPECT system is able to obtain 75 non-overlapping projections in one shot and used for reconstructing high resolution images. However, since each pinhole on the cylindric pinhole collimator is a micro aperature that is formed with a width smaller than 1 millimeter, such cylindric pinhole collimator can be very expensive and difficult to build.

Therefore, it is in need of a low-cost, easy-to-build, high-resolution SPECT scanner and the operating method thereof.

TECHNICAL SUMMARY

The present disclosure relates to a single photon emission computed tomography (SPECT) instrument and the operating method thereof, in which the single photon emission computed tomography instrument is operated basing upon the use of a plurality of beam stoppers, that are made of a material of high atomic number and high density, for absorbing beams of radiation during the proceeding of an imaging process, and during the imaging process when an object is being scanned at different angles, the plural beam stoppers can be installed into first and then being removed from the SPECT instrument so as to obtain projection datasets of different detection angles respectively corresponding to the situation where there are beam stoppers and the situation where there is no beam stopper, and thereafter, by subtracting the projection datasets of the same detection angle that are obtained from the situation with beam stoppers and the situation without beam stoppers, calibrated projection datasets of different detection angles that are resulting from beams of radiations emitted from a specific FOV can be obtained and used in an image reconstruction algorithm for obtaining a high resolution SPECT image.

In an exemplary embodiment, the present disclosure provides a single photon emission computed tomography (SPECT) instrument, comprising: a platform; at least one detector, each disposed at one side of the platform; at least one beam stopper, each disposed at a position between the platform and the at least one detector; a signal processing device, electrically connected to the at least one detector for communicated with the same; and a computing device, electrically connected to the signal processing device for communicated with the same.

In another exemplary embodiment, the present disclosure provides an operating method adapted for scanning an object using a single photon emission computed tomography (SPECT) instrument that is configured with at least one beam stopper, comprising the steps of: removing the at least one beam stopper from the SPECT instrument while enabling the same to scan the object in at least one detection angle for obtaining a projection dataset without the beam stopper; installing the at least one beam stopper into the SPECT instrument while enabling the same to scan the object in the at least one detection angle for obtaining another projection dataset with the beam stopper; subtracting the projection dataset without the beam stopper from that with the beam stopper so as to obtain a calibrated projection dataset; and using the calibration projection dataset for the reconstruction of cross sections of the object.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DESCRIPTION OF THE EXEMPLARY EMBODIMENTS

For your esteemed members of reviewing committee to further understand and recognize the fulfilled functions and structural characteristics of the disclosure, several exemplary embodiments cooperating with detailed description are presented as the follows.

Figure 1:
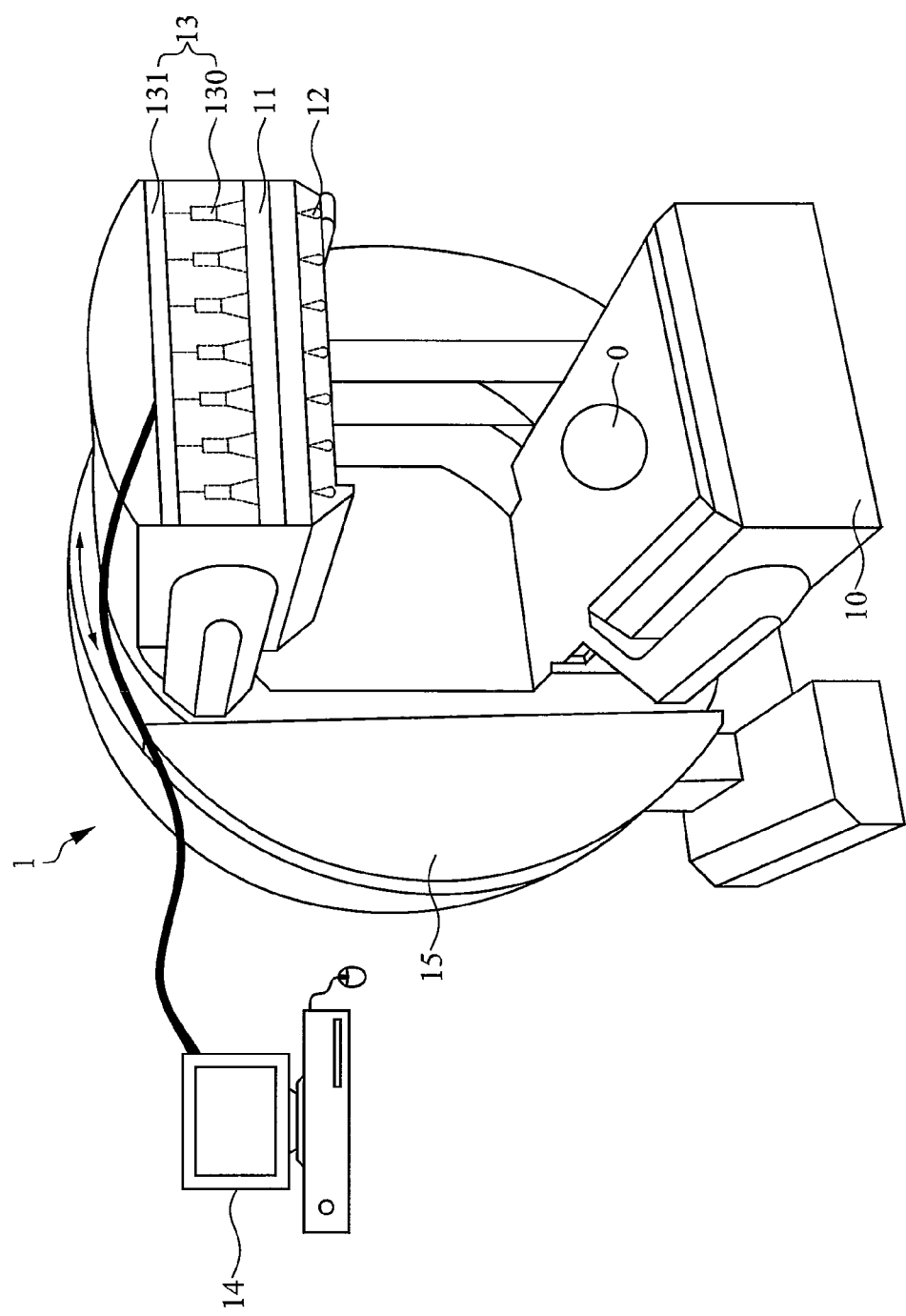
FIG. 1 is a schematic diagram showing a SPECT instrument according to a first embodiment of the present disclosure.

Please refer to FIG. 1, which is a schematic diagram showing a SPECT instrument according to a first embodiment of the present disclosure. In FIG. 1, the present disclosure provides a single photon emission computed tomography (SPECT) instrument 1, which comprises: a platform 10; at least one detector 11, each disposed at one side of the platform 10; at least one beam stopper 12, each disposed at a position between the platform 10 and the at least one detector 11; a signal processing device 13, electrically connected to the at least one detector 11 for communicated with the same; and a computing device 14, electrically connected to the signal processing device 13 for communicated with the same. In addition, the signal processing device 13 further comprises: a signal conversion/amplification unit 130 and a signa; filtering unit 131. In this embodiment the signal conversion/amplification unit is substantially a photomultiplier tube, and the signal filtering unit is substantially an energy discrimination and positioning electronics, in that the photomultiplier tube is used for amplifying the electric signals from the detector 11 by several hundred thousand times; and the energy discrimination and positioning electronics is provided for estimating the position where is most likely to be stricken by photons and thus making an evaluation to determine whether the energy of those photons is within a specific range, and if any photon whose energy level is determined to be too low, it will be categorized as scattered photon and will not be accounted for, otherwise, it will be categorized as a useful photon. Moreover, as the computing device 14 is used for processing data outputted from the signal processing device 13, it is generally being embedded with a filtered back-projection algorithm or a maximum likelihood expectation maximization algorithm to be used for the reconstruction of cross sections of a scanned object 0.

In this embodiment, the beam stopper 12 is movably arranged at a position between the detector 11 and the platform 10, by that the beam stopper 12 can be detached easily and removed from the SPECT instrument 1 at will if required. Consequently, not only the SPECT instrument is able to switch between "scanning with beam stopper" and "scanning without beam stopper" easily according to actual requirement, but also the beam stopper 12 can be moved to any position that is specified by users. For instance, the beam stopper 12 can be moved to a position for allowing the distance between the detector 11 and the beam stopper 12 to be larger than that of the beam stopper 12 and the scanned object 0, resulting that the reconstructed image is amplified. It is noted that although there are more than one beam stoppers 12 used in the embodiment shown in FIG. 1, it is feasible to have only one beam stopper 12 in the SPECT instrument, and thus the amount of beam stopper 12 used in the SPECT instrument is not limited by the embodiment of FIG. 1.

Operationally, a user is able to operate the SPECT instrument 1 for scanning the scanned object 0 in any detection angle at will, with or without the beam stopper 12. That is, images of the scanned object 0 at different angles that are acquired with beam stopper 12 installed and without beam stopper 12 detached can be obtained using the SPECT instrument 1. Thereafter, by subtracting the projection dataset without the beam stopper from that with the beam stopper, a calibrated projection dataset is obtained and used in an image reconstruction algorithm so as to obtain a high resolution image relating to the radioactivity distribution inside the object 0. For facilitating the acquisition of images in different detection angles, the SPECT instrument 1 in this embodiment further comprises: a rotary frame 15, which is provided for the detector 11 and the beam stoppers 12 to mount thereat for allowing those to orbit around the platform 10. As the main function of the beam stoppers 12 is to absorb beams of radiation during the proceeding of SPECT imaging, the beam stoppers 12 are generally made of a material of high atomic number and high density. In this embodiment, the beam stopper 12 is made of tungsten, but is not limited thereby.

Figure 2:
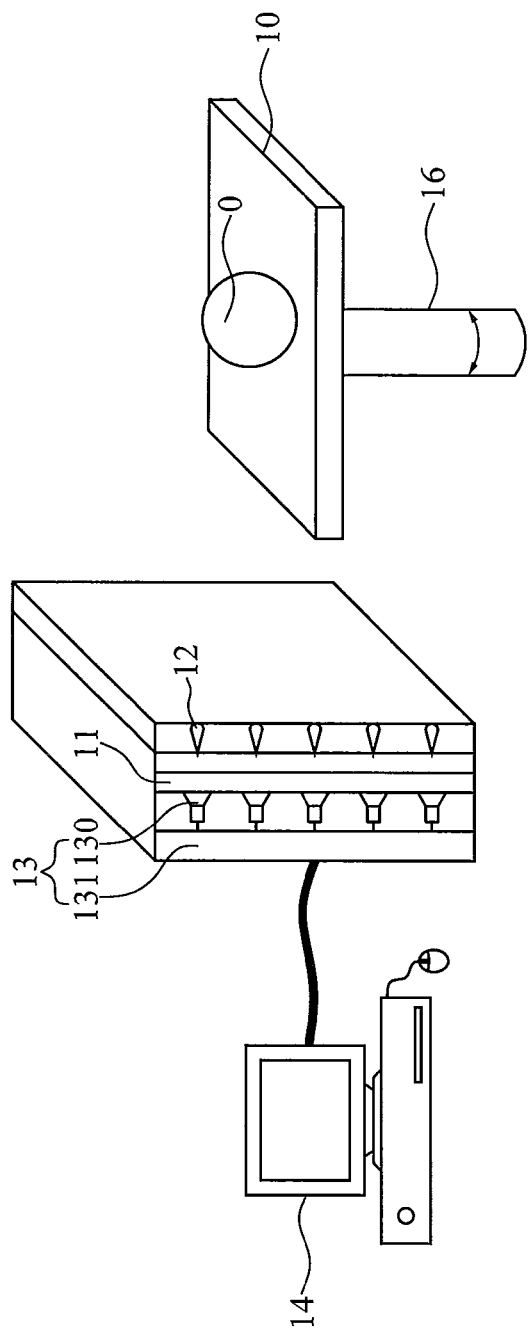
FIG. 2 is a schematic diagram showing a SPECT instrument according to a second embodiment of the present disclosure.

Please refer to FIG. 2, which is a schematic diagram showing a SPECT instrument according to a second embodiment of the present disclosure. In this embodiment, the SPECT instrument further comprises: an actuator 16, which is coupled to the platform 10 for driving the same to rotate. Thus, the different between the second embodiment and the first embodiment is that: the detector 11 and the beam stoppers 12 in the first embodiment of FIG. 1 are brought along to rotate around the platform 10 by the rotary frame 15, whereas the platform 10 itself can be driven to rotate by the actuator 16 for facilitating the acquisition of images of the scanned object 0 at various detection angles.

Figure 3:
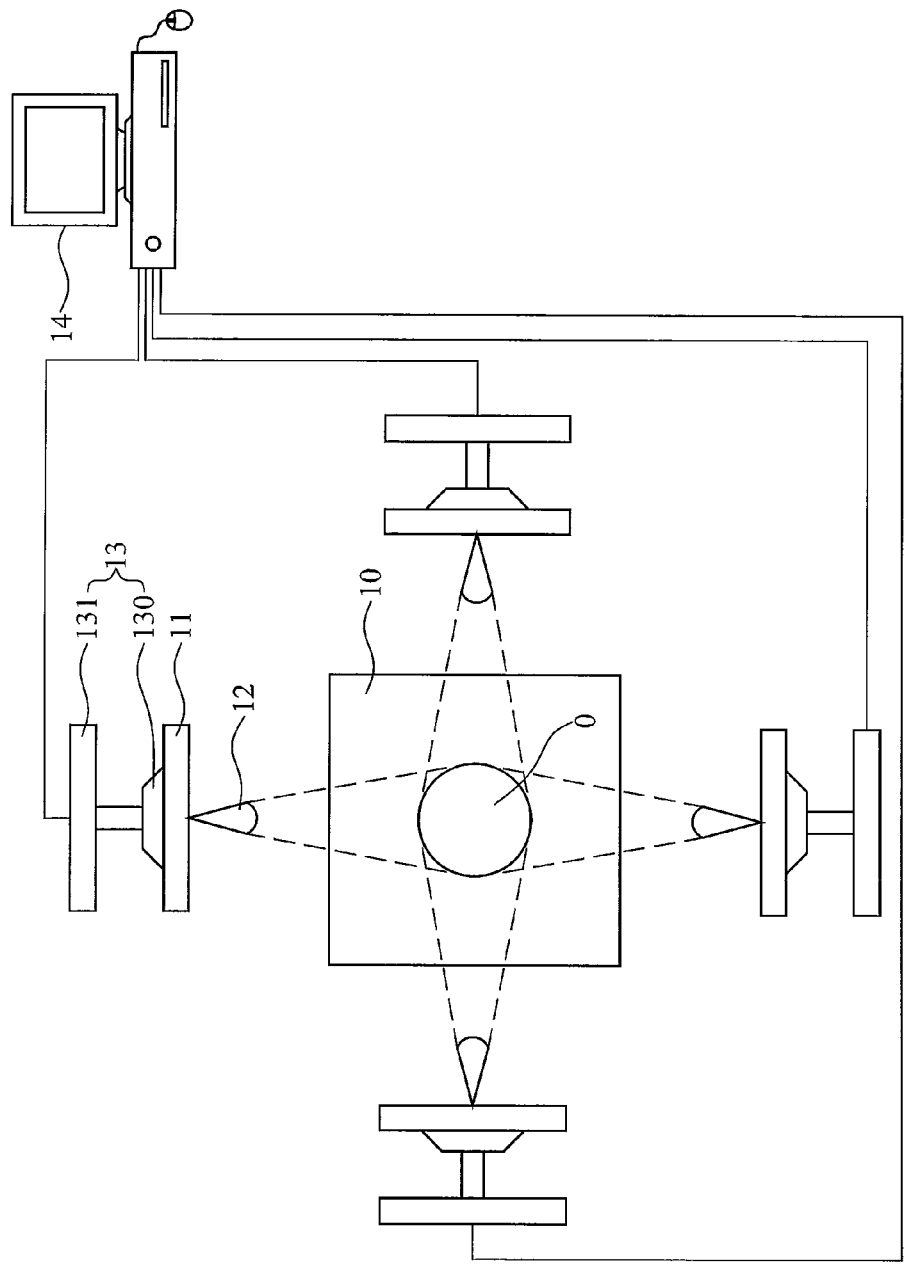
FIG. 3 is a schematic diagram showing a SPECT instrument according to a third embodiment of the present disclosure.

Please refer to FIG. 3, which is a schematic diagram showing a SPECT instrument according to a third embodiment of the present disclosure. In this embodiment, instead of only one detection assembly, there are more than one detection assemblies being included in the SPECT instrument that are respectively disposed surrounding the scanned object 0 so as to acquire images of the scanned object respectively at a specific detection angle, whereas each detection assembly is comprised of: at least one beam stopper 12, at least one detector 11 and a signal processing device 13. Moreover, each signal processing device 13 is connected to a computing device 14 so as to transmit the scanning result to the computing device 14 for processing. As the embodiment shown in FIG. 3, there are four sets of detection assemblies being included in the SPECT instrument, however, it is noted that the amount of detection assembly as well as the distance between any two neighboring detection assemblies and the respective distance between each detection assembly and the scanned object are not limited thereby. Thus, operationally, the beam stoppers can be move to any position at will for varying their FOV so as to have a larger sampling space, and thereby, a clear SPECT image of the scanned object can be reconstructed and obtained without having the detection assemblies to orbit around the scanned object 0.

Figure 4:
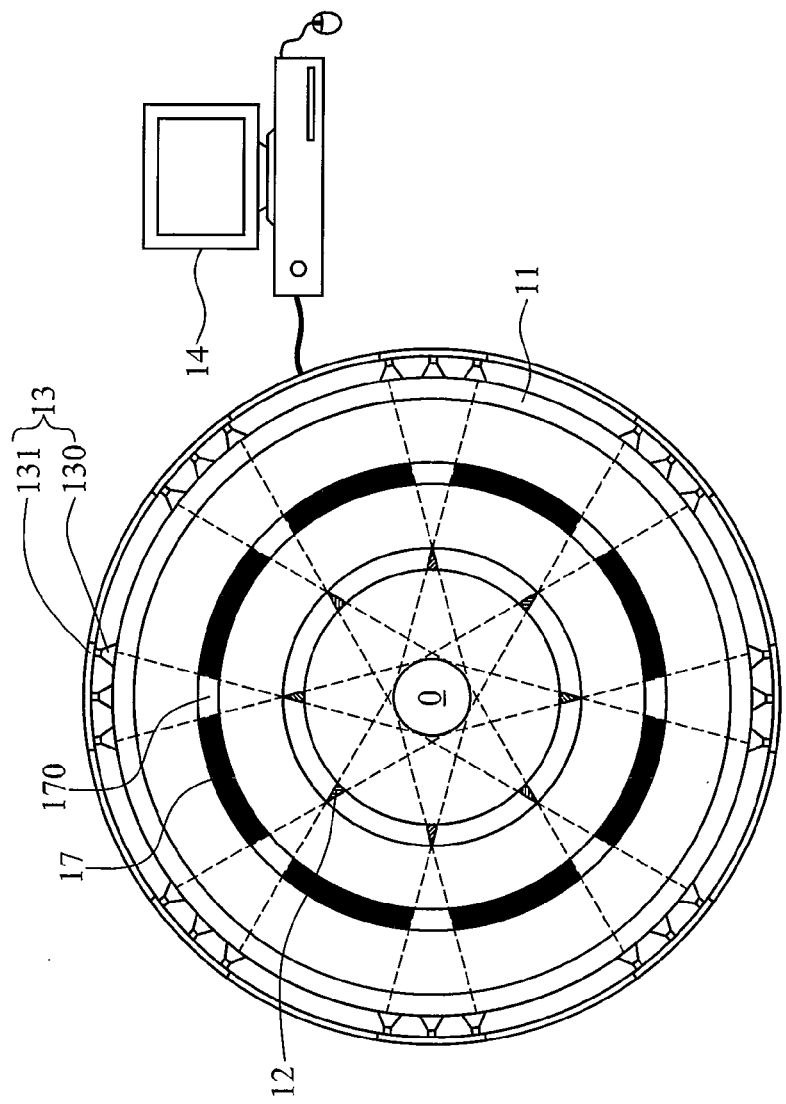
FIG. 4 is a schematic diagram showing a SPECT instrument according to a fourth embodiment of the present disclosure.

Please refer to FIG. 4, which is a schematic diagram showing a SPECT instrument according to a fourth embodiment of the present disclosure. In this embodiment, there are a plurality of beam stoppers 12 being disposed into a ring-shaped formation surrounding the scanned object 0 while allowing the scanned object 0 to be positioned at the center of the ring-shaped formation. In the embodiment shown in FIG. 4, as the plural beam stoppers 12 are uniformly embedded on the wall of a hollow cylinder, the plural beam stoppers 12 are disposed into a ring-shaped formation surrounding the scanned object 0. Moreover, for enabling beams of radiation can only be absorbed by those beam stoppers 12, the hollow cylinder should be made of a material of low atomic number and low density. In this embodiment, the hollow cylinder is made of carbon fiber, but is not limited thereby. In addition, the arrangement of the plural beam stoppers 12 is also not being limited to the ring-shaped formation. For perverting projection overlapping, any two neighboring beam stoppers 12 should be spaced from each other by a specific interval. In FIG. 4, the SPECT instrument further comprises: a shielding 17, which is substantially a hollow cylinder having a plurality of opening 170 formed on the cylinder wall while being disposed outside the formation of the plural beam stoppers 12. By the arrangement of the shielding 17, any noise radiation is prevented from being detected by the detectors 11, that is, any beam of radiation that is not originated from the FOV, i.e. the scanned object, will be blocked. Thus, the shielding 17 should be made of a heavy metal. In this embodiment, the shielding 17 is made of tungsten, but is not limited thereby. It is noted that each opening 170 on the cylinder wall of the shielding 17 should be located exactly at a position corresponding to one beam stopper 12 for allowing the radiation beams of FOV whichever travels passing the blocking of the corresponding beam stopper 12 to travel therethrough and thus project on the a designated projection area while striking on the detectors 11 distributed within the designated projection area. In this embodiment, there is a plurality of detectors 13 that are embedded on the wall of a hollow cylinder whereas the hollow cylinder is arranged ensheathing the shielding 17. However, the formation of the detectors 13 is not limited thereby, and thus can be embedded on the planar walls of a column with polygon cross section. In this embodiment, by the cooperation of the beam stoppers 12, the openings 170 on the shielding 17, the radiation beams from the FOV will strike on detectors 13 that are located at different angular angles with respected to the scanned object 0, and thereby, the SPECT instrument is able to acquire projection datasets of different detection angles without having to enable any type of rotation movement, and also the SPECT instrument is able to obtain a high resolution SPECT image of the scanned object from the reconstruction of the projection datasets.

Figure 5B:
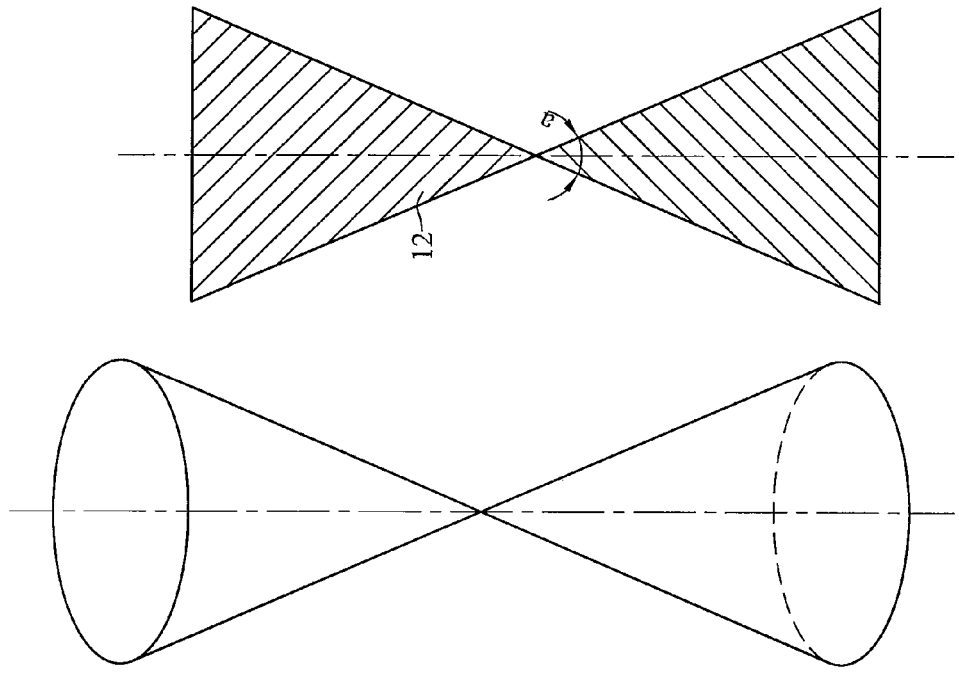
FIG. 5A, FIG. 5B and FIG. 5C are schematic diagrams showing three different beam stoppers for the present disclosure.
Figure 5A:
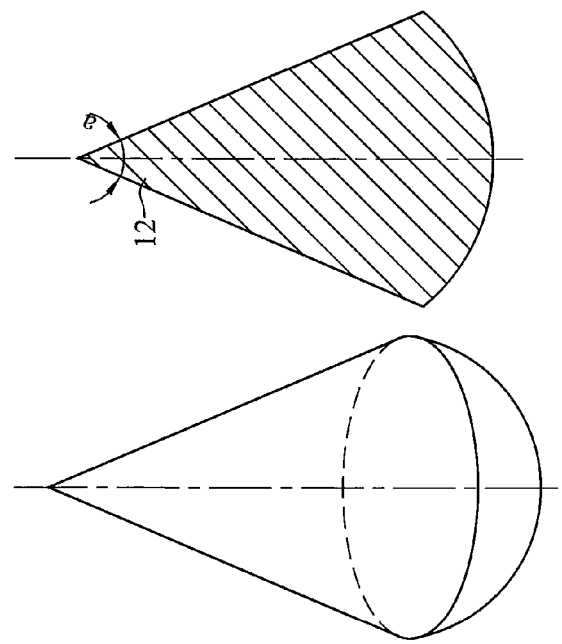

Basically, the resolution of a SPECT image can be significantly affected by and depended upon the shape of the beam stopper 12 used in the SPECT instrument. Please refer to FIG. 5A, FIG. 5B and FIG. 5C, which are schematic diagrams showing three different beam stoppers for the present disclosure. In FIG. 5A, the beam stopper 12 is formed as a cone with an arc-shaped bottom. As the cross section of the cone-shaped beam stopper 12 is a shaped like a fan, it is known that by narrowing the included angle of the fan, the resolution of the SPECT image can be increased. In FIG. 5B, the beam stopper 12 is formed as an assembly of two oppositely disposed cones with their tips connected to each other. As the beam stoppers 12 shown in FIG. 5A and FIG. 5B are formed in a shape opposite to that of pinhole collimator since the arrangement of pinhole collimator is to allow the radiation beam to travel passing only through the pinholes thereof, while the arrangement of the beam stoppers 12 is to absorb any radiation beams projected thereon. Accordingly, during the performing of an imaging process for scanning an object at different detection angles, the beam stoppers can be installed into first and then being removed from the SPECT instrument so as to obtain projection datasets of different detection angles respectively corresponding to the situation where there are beam stoppers and the situation where there is no beam stopper, and thereafter, by subtracting the projection datasets of the same detection angle that are obtained from the situation with beam stoppers and the situation without beam stoppers, a calibrated projection datasets of different detection angles that are similar to those obtained from conventional SPECT interment using pinhole collimator, but under a comparatively much lower cost.

Figure 5C:
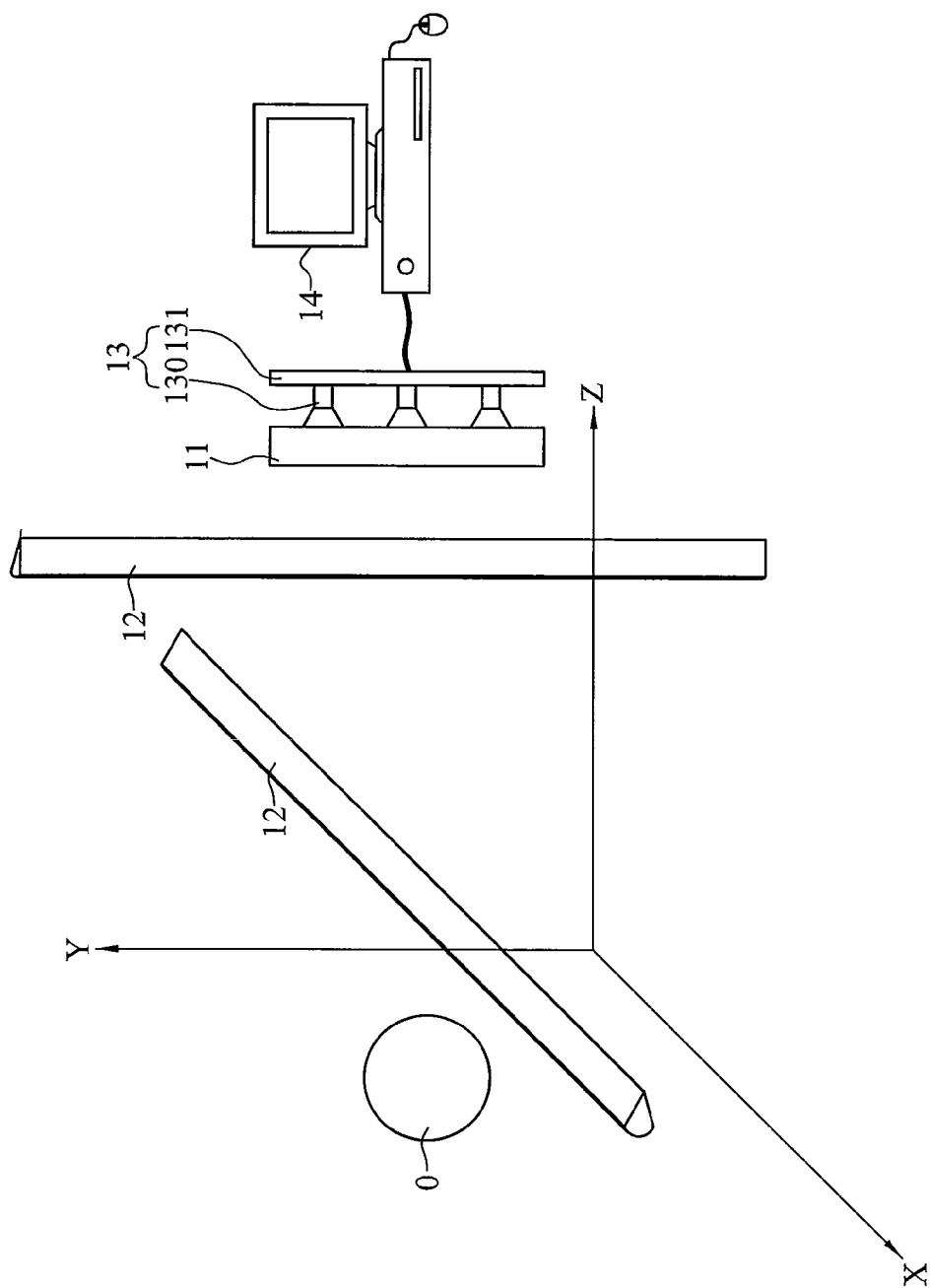

In FIG. 5C, the beam stoppers are substantially two bar-like beam stoppers 12 that arranged perpendicular to each other without intersecting while allowing the distance between one bar-like beam stopper 12 and the scanned object 0 to be different from the distance between another bar-like beam stoppers 12 and the scanned object 0. Hence, the amplification in longitudinal axis and horizontal axis of the detector 11 upon the scanned object 0 can be adjusted by the changing of the distance between the two bar-like beam stoppers 12. Moreover, the cross section of the bar-like beam stopper 12 is formed in a shape selected from the group consisting of: a fan and a triangle.

Figure 6:
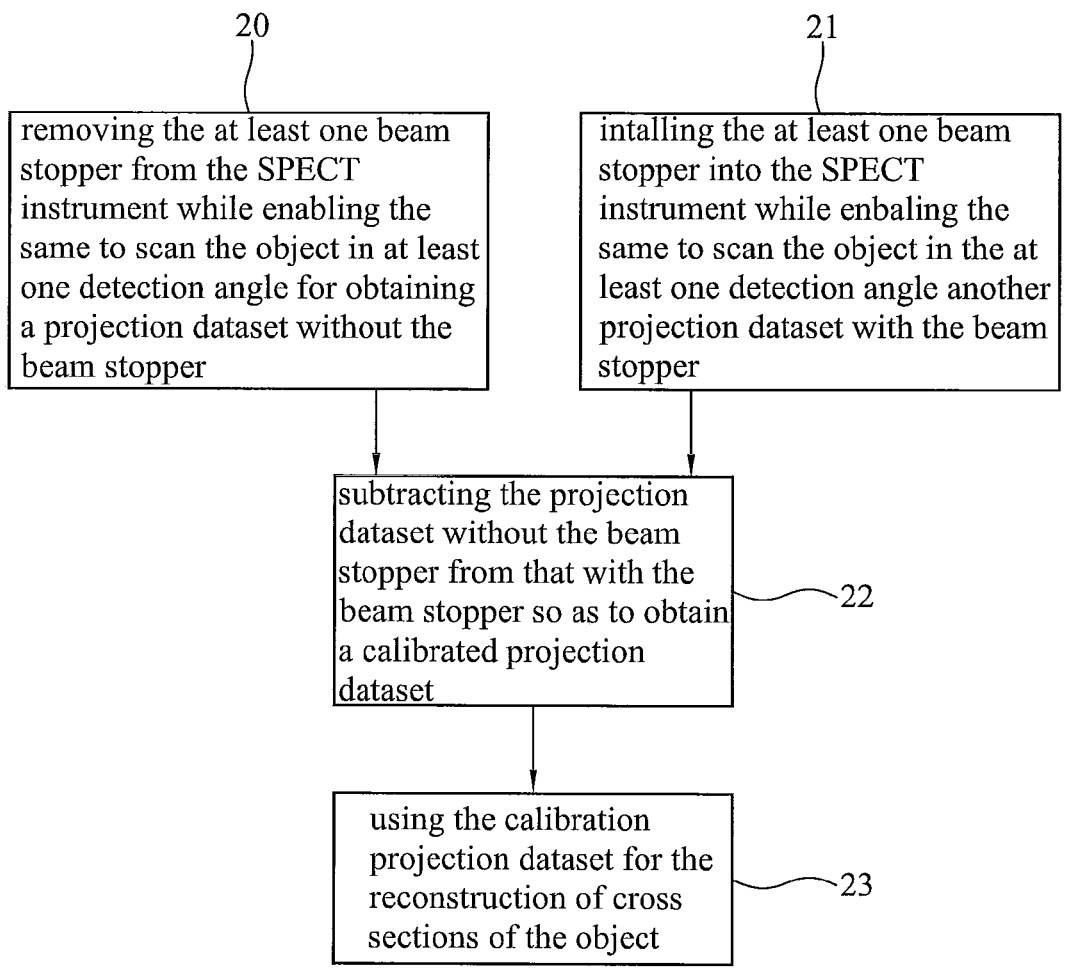
FIG. 6 is a flow chart depicting steps performed in a SPECT imaging method of the present disclosure.

Please refer to FIG. 6, which is a flow chart depicting steps performed in a SPECT imaging method of the present disclosure. The SPECT imaging method 2 shown in FIG. 6 is adapted for scanning an object using a single photon emission computed tomography (SPECT) instrument 1 that is configured with at least one beam stopper 12, comprising the steps of removing the at least one beam stopper from the SPECT instrument while enabling the same to scan the object in at least one detection angle for obtaining a projection dataset without the beam stopper, as the step 20 shown in FIG. 6; installing the at least one beam stopper into the SPECT instrument while enabling the same to scan the object in the at least one detection angle for obtaining another projection dataset with the beam stopper, as the step 21 shown in FIG. 6; subtracting the projection dataset without the beam stopper from that with the beam stopper so as to obtain a calibrated projection dataset, as the step 22 shown in FIG. 6; and using the calibration projection dataset for the reconstruction of cross sections of the object, as the step 23 shown in FIG. 6. Generally, the reconstruction of cross sections of the object is performed using an algorithm selected from the group consisting of: a filtered back-projection algorithm and a maximum likelihood expectation maximization (ML-EM) algorithm.

Comparing with those conventional SEPCT instrument using pinhole collimator, and in addition to the ability to acquire high resolution images, the SPECT instrument of the present disclosure is lighter and smaller in volume, easier to build and lower in manufacturing cost since it uses less material of high atomic number and high density. Moreover, since most beam stoppers are built light and handy, they can be move easily to any locations at will during the performing of an imaging process according to the shape of the scanned object or for obtaining a specific degree of amplification in the reconstructed image. Thus, the SPECT instrument using beam stoppers is comparatively more user friendly.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A single photon emission computed tomography (SPECT) instrument, comprising:
   a platform;
   at least one detector, each disposed at one side of the platform;
   at least one beam stopper, each disposed at a position between the platform and the at least one detector;
   a signal processing device, electrically connected to the at least one detector for communicated with the same; and
   a computing device, electrically connected to the signal processing device for communicated with the same,
   wherein the at least one beam stopper is configured to absorb beams of radiation during proceeding of SPECT imaging, and
   wherein each beam stopper is formed as an assembly of two oppositely disposed cones with their tips connected to each other.

2. The SPECT instrument of claim 1, further comprising: a rotary frame, provided for the at least one detector and the at least one beam stopper to mount thereat for allowing those to orbit around the platform.

3. The SPECT instrument of claim 1, further comprising: an actuator, coupled to the platform for driving the same to rotate.

4. The SPECT instrument of claim 1, wherein the at least one detector is formed as a ring surrounding the platform, and there are a plurality of beam stoppers being disposed into a ring-shaped formation at a position between the at least one detector and the platform.

5. The SPECT instrument of claim 4, further comprising: a shielding, being a hollow cylinder having a plurality of opening formed on the cylinder wall while being disposed at a position between the plural beam stoppers and the at least on detector.

6. The SPECT instrument of claim 1, wherein the at least one beam stopper is movably arranged at a position between the at least one detector and the platform.

7. The SPECT instrument of claim 1, wherein the at least one beam stopper is made of a material of high atomic number.

8. The SPECT instrument of claim 7, wherein the material of high atomic number is tungsten.

9. The SPECT instrument of claim 1, wherein each beam stopper is formed as a cone with an arc-shaped bottom.

10. The SPECT instrument of claim 1, wherein the signal processing device further comprises: a signal conversion/amplification unit and a signal filtering unit.

11. The SPECT instrument of claim 10, wherein the signal conversion/amplification unit is substantially a photomultiplier tube, and the signal filtering unit is substantially an energy discrimination and positioning electronics.

12. The SPECT instrument of claim 1, wherein there are two bar-like beam stoppers in the SPECT instrument that arranged perpendicular to each other without intersecting.

13. The SPECT instrument of claim 12, wherein the cross section of the bar-like beam stopper is formed in a shape selected from the group consisting of: a fan and a triangle.

14. An operating method adapted for scanning an object using a single photon emission computed tomography (SPECT) instrument that is configured with at least one beam stopper, the method comprising the steps of:
   removing the at least one beam stopper from the SPECT instrument while enabling the same to scan the object in at least one detection angle for obtaining a projection dataset without the beam stopper;
   installing the at least one beam stopper into the SPECT instrument while enabling the same to scan the object in the at least one detection angle for obtaining another projection dataset with the beam stopper, wherein the at least one beam stopper is configured to absorb beams of radiation during proceeding of SPECT imaging;
   subtracting the projection dataset without the beam stopper from that with the beam stopper so as to obtain a calibrated projection dataset; and
   using the calibration projection dataset for the reconstruction of cross sections of the object,
   wherein each beam stopper is formed as an assembly of two oppositely disposed cones with their tips connected to each other.

15. The method of claim 14, wherein the reconstruction of cross sections of the object is performed using an algorithm selected from the group consisting of: a filtered back-projection algorithm and a maximum likelihood expectation maximization (ML-EM) algorithm.

* * * * *